US010265302B2

United States Patent
Lejeune et al.

(10) Patent No.: US 10,265,302 B2
(45) Date of Patent: Apr. 23, 2019

(54) COMPOUND USEFUL FOR THE TREATMENT OF NONSENSE-MUTATION-MEDIATED DISEASES AND PHARMACEUTICAL COMPOSITION COMPRISING SAID COMPOUND

(71) Applicants: UNIVERSITE DE LILLE, Lille (FR); INSTITUT NATIONAL DE LA SANTE ET DE LA RECHERCHE MEDICALE (INSERM), Paris (FR); INSTITUT PASTEUR DE LILLE, Lille (FR)

(72) Inventors: Fabrice Lejeune, Tourcoing (FR); Benoit Deprez, Lille (FR); Terence Beghyn, Haubourdin (FR); Sara Sofia Gonzalez-Hilarion, Lille (FR)

(73) Assignees: UNIVERSITE DE LILLE, Lille (FR); INSTITUT NATIONAL DE LA SANTE ET DE LA RECHERCHE MEDICALE (INSERM), Paris (FR); INSTITUT PASTEUR DE LILLE, Lille (FR)

(*) Notice: Subject to any disclaimer, the term of this patent is extended or adjusted under 35 U.S.C. 154(b) by 0 days.

(21) Appl. No.: 15/882,548

(22) Filed: Jan. 29, 2018

(65) Prior Publication Data
US 2018/0147191 A1 May 31, 2018

Related U.S. Application Data

(63) Continuation of application No. 13/813,914, filed as application No. PCT/EP2011/063126 on Jul. 29, 2011, now Pat. No. 9,913,829.

(30) Foreign Application Priority Data

Aug. 5, 2010 (FR) ...................... 10 56472

(51) Int. Cl.
A61K 31/436 (2006.01)
A61K 31/35 (2006.01)
A61K 31/122 (2006.01)
A61K 31/435 (2006.01)
A61K 31/4245 (2006.01)

(52) U.S. Cl.
CPC .......... *A61K 31/436* (2013.01); *A61K 31/122* (2013.01); *A61K 31/35* (2013.01); *A61K 31/4245* (2013.01); *A61K 31/435* (2013.01)

(58) Field of Classification Search
CPC .................................................. A61K 31/122
See application file for complete search history.

(56) References Cited

U.S. PATENT DOCUMENTS

| 8,716,321 | B2 | 5/2014 | Hirawat et al. |
| 2007/0135473 | A1 | 6/2007 | Semov et al. |
| 2011/0003843 | A1 | 1/2011 | Lejeune et al. |
| 2012/0125325 | A1 | 5/2012 | Bannister et al. |

FOREIGN PATENT DOCUMENTS

| WO | 2004091502 | 10/2004 |
| WO | 2008021210 | 2/2008 |
| WO | 2008101935 | 8/2008 |
| WO | 2009151569 | 12/2009 |
| WO | 2010139985 | 12/2010 |

OTHER PUBLICATIONS

International Search Report issued in International Application No. PCT/EP2011/063126 dated Aug. 26, 2011 (4 pages).
Conti et al., "Nonsense-mediated mRNA decay: molecular insights and mechanistic variations across species", Current Opinion in Cell Biology, 2005, vol. 17, pp. 316-325.
Kang et al., "Making sense of nonsense GABAA receptor mutations associated with genetic epilepsies", Cell Press, Trends in Molecular Medicine, 2009, vol. 15, No. 9, pp. 430-438.
Maquat, "Nonsense-mediated mRNA decay: splicing, translation and mRNP dynamics". Nature Reviews, Molecular Cell Biology, Feb. 2004, vol. 5, pp. 89-99.
Rossi et al., "Identification of inactivating mutations in the JAK1, SYNJ2 and CLPTM1 genes in prostate cancer cells, using inhibition of nonsense-mediated decay and microarray analysis", Cancer Genetics and Cytogenetics, 2005, vol. 161, pp. 97-103.
Higuchi et al., "Molecular Defects in Hemophilia A: Identification and Characterization of Mutations in the Factor VIII Gene and Family Analysis", Blood, Aug. 15, 1989, vol. 74, No. 3, pp. 1045-1051.
Wilton et al., "Revertant fibres: a possible genetic therapy for Duchenne muscular dystrophy", Neuromuscular Disorders, 1997, vol. 7, pp. 329-335.
Du et al., "PTC124 is an orally bioavailable compound that promotes suppression of the human CFTR-G542X nonsense allele in a CF mouse model", Feb. 12, 2008, vol. 105. No. 6, pp. 2064-2069.

*Primary Examiner* — Yong S. Chong
(74) *Attorney, Agent, or Firm* — Hamre, Schumann, Mueller & Larson, P.C.

(57) ABSTRACT

The present invention relates to the compound of formula (I)

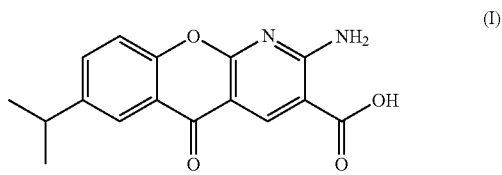

for use in the treatment of a nonsense-mutation-mediated genetic disease.

7 Claims, 9 Drawing Sheets

COMPOUND USEFUL FOR THE TREATMENT OF NONSENSE-MUTATION-MEDIATED DISEASES AND PHARMACEUTICAL COMPOSITION COMPRISING SAID COMPOUND

The present invention relates to a compound used for treating, preventing or diagnosing a genetic disease caused by a nonsense mutation also called "nonsense-mutation-mediated disease". The present invention also relates to a pharmaceutical composition comprising the above-mentioned compound. The present invention further relates to a method for determining the presence of a nonsense mutation in a given gene.

A nonsense mutation is a genetic in-frame mutation leading to the transformation of a sense codon into a premature stop codon in the messenger RNA (hereinafter mRNA). A premature stop codon (hereinafter PTC) is defined as a stop codon located in the coding sequence of a gene, upstream from the normal stop codon. The normal stop codon stops the gene translation and enables a full-length wild type protein synthesis. The PTC prevents the wild-type protein synthesis and leads to the silencing of the mutated gene. The lack of protein (partial or total lack) leads to the pathology. For example, a PTC in the gene coding for the dystrophin protein causes nonsense-mutation-mediated-Duchenne Muscular Dystrophy in boys.

It is known that nonsense-mutation-mediated prostatic cancers are caused by a PTC in JAK1, SYNJ2 or CLPTM1 genes (see "Identification of inactivating mutations in the JAK1, SYNJ2 and CLPTM1 genes in prostate cancer cells, using inhibition of nonsense-mediated decay and microarray analysis" in Cancer genetics and cytogenetics (2005)). It is also known that nonsense-mutation-mediated epilepsy is caused by PTC in $GABA_A$ receptor subunit gene (see "Making sense of nonsense $GABA_A$ receptor mutations associated with genetic epilepsies" in Cell (2010)).

Document WO 2008/101935 discloses compounds useful for treating nonsense-mutation-mediated diseases. The compounds disclosed in this document are indole derivatives and have been tested on HeLa cancerous cells previously transfected with two plasmids and on two lymphoblastic cell-lines coming from DMD (Duchene muscular dystrophy) patients. Document WO 2004/091502 discloses compounds useful in the treatment of genetic diseases caused by a PTC coming from a nonsense mutation. One of the compounds disclosed in WO 2004/091502 (ataluren) is currently studied in a phase 2a clinical trial as an oral treatment for nonsense-mutation-mediated hemophilia A and B, in a phase 2 trial in nonsense-mutation-mediated Methylmalonic Acidemia and in a phase 3 trial in subjects with nonsense-mutation-mediated cystic fibrosis. A phase 2a trial in subjects with nonsense-mutation-mediated Duchenne/Becker muscular dystrophy has been already completed.

One purpose of the present invention is to provide a compound enabling the treatment of genetic diseases, caused by a nonsense mutation.

Accordingly, the present invention provides the compound of formula (I)

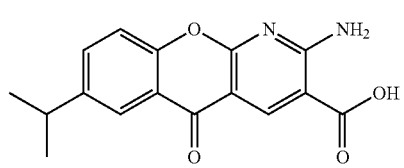

or a salt, solvate, clathrate, hydrate or polymorph thereof for use in the treatment or the prophylaxis of a genetic disease, said genetic disease being a nonsense-mutation-mediated disease.

The compound of Formula (I) ((2-amino-7-isopropyl-5-oxo-5H-chromeno[2,3-b]pyridine-3-carboxylic acid) is commonly called amlexanox. It is currently used as therapeutic agent for the treatment of asthma and allergic rhinitis when administered orally, and for the treatment of canker sores when used topically.

It is also used for the treatment of aphthous ulcer (Aphthasol®). It is known for its anti-inflammatory and anti-allergic properties. It is also used in the treatment of bronchic asthma. Its safety profile is well known.

WO2009/151569 relates to a method of treating a B-cell proliferative disorder by administering to a patient a BAR agonist (Beta(2)-adrenergic receptor). The BAR agonist may be administered as a monotherapy or in combination with one or more other agents, like a PDE enzyme inhibitor. The compound according to the invention is cited in a long list of compounds as a PDE inhibitor. WO2009/151569 does not indicate or suggest that a genetic mutation is implicated in the aforementioned proliferative mechanism.

WO 2008/021210 relates to a method for treating a neurodegenerative disorder using compounds listed in various tables. The compound according to the present invention is disclosed in table 1a as an antihistamine (H1), a leukotriene receptor antagonist, an antiallergic and an anti-inflammatory. WO 2008/021210 does not disclose nor suggest that a genetic mutation plays a role in the treated diseases.

Document WO 2010/139985 discloses the use of the compound according to the present invention for treating a disease associated with neutrophilia. Neutrophilia is a term used for a patient condition when said patient has a high number of neutrophil granulocytes in his blood. Neutrophils are the most abundant type of white blood cells in mammals. Neutrophils are associated with inflammatory diseases. Neutrophils are the first response in the inflammatory process, particularly, in bacterial infection, environmental exposure and some cancers. WO 2010/139985 does not disclose nor suggest the use of the above-mentioned compound for the treatment of a nonsense-mutation-mediated disease.

Moreover, document US 2007/0135473 discloses the use of the compound according to the present invention for treating diseases associated with tumor cells which express one or more proteins of S100 family. The above-mentioned compound is considered as effective in retarding the progression and/or the metastasis of these tumors. S100 proteins have been implicated in a variety of intracellular and extracellular functions. S100 proteins are involved in regulation of protein phosphorylation, transcription factors, Ca++ homeostasis, the dynamics of cytoskeleton constituents, enzyme activities, cell growth and differentiation, and the inflammatory response. However, US 2007/0135473 does not disclose nor suggest the use of the compound of Formula (I) for the treatment of a nonsense-mutation-mediated disease. Further, there is no evidence that S100 proteins are involved in a disease caused by a nonsense-mutation.

The Applicants have discovered that the compound of Formula (I) is able to inhibit nonsense-mediated mRNA decay (hereinafter called NMD) and/or has a readthrough effect, depending on mutated genes, as explained hereinafter. Accordingly, the compound of the invention enables functional protein synthesis.

Theoretically, when a PTC is present on an mRNA, ribosomes should synthesize a truncated protein. Truncated proteins have a shorter peptide chain compared to wild-type proteins. A wild-type protein is defined as a protein synthesized when the corresponding gene does not comprise any mutations. Truncated proteins may be functional or not. In other words, truncated proteins may produce or not the same effects on cells or entire body as the effects produced by wild-type proteins. mRNAs containing a PTC are eradicated by the organism before steady-state translation occurs. This PTC-containing mRNA decay is also called nonsense-mediated mRNA decay (NMD). NMD is a natural qualitative surveillance mechanism existing in all eukaryote organisms. NMD aims the degradation of PTC-containing mRNAs.

In some cases, the truncated protein that would come from the translation of a nonsense-mutation containing gene would be functional. The truncated-protein functionality may occur despite the fact that the truncated protein is shorter than the wild type protein. In other words, even if the truncated protein is different from the wild-type one, it may produce in cells and organism the same effects as those produced by the wild-type protein. In these cases, the truncated proteins produce the wild-type phenotype. Consequently, in this case, if NMD is inhibited, the functional truncated proteins stay in the cell and have the same function in the cell and thus organism as the wild-type protein, just as if the corresponding gene does not harbor any nonsense mutation.

NMD mechanism is well known and described in several publications (See Conti, E. and E. Izaurralde, *Nonsense-mediated mRNA decay: molecular insights and mechanistic variations across species*. Curr Opin Cell Biol, 2005. 17(3): p. 316-25 and Maquat, L. E., *Nonsense-mediated mRNA decay: splicing, translation and mRNP dynamics*. Nat Rev Mol Cell Biol, 2004. 5(2): p. 89-99.

It is known that under specific conditions, despite the presence of a termination codon (premature or not) harbored in mRNA, ribosome keeps on translating said mRNA into protein by incorporating an amino-acid at the stop codon position. This phenomenon is called "readthrough". The amino acid incorporated at the nonsense position can be identical to the amino acid present in the wild-type protein or different. Therefore, the resulting protein may be functional or not depending on the role of the amino acid located at the nonsense position, for the protein function.

In the last years, there has been an attempt to develop pharmacological approaches for mutations generating in-frame PTCs. These therapeutic approaches are aimed at promoting translational readthrough of the PTCs, to enable the synthesis and expression of full-length functional proteins at sufficient levels. In most of these studies, the readthrough drugs were aminoglycosides, mainly gentamicin. The clinical benefit of gentamicin is limited since high concentrations and/or long-term treatments have severe side effects such as kidney damage and loss of hearing. Recently, PTC124 or ataluren has been identified as a small organic compound able to promote readthrough of PTCs. WO2004/091502 discloses PTC124 and 1,2,4-oxadiazole benzoic acid derivatives.

According to the present invention, "NMD inhibition" means partial or total inhibition of NMD and "PTC readthrough" means partial or total readthrough of PTC. It has been found that the compound according to the invention has a readthrough effect. The compound according to the invention can therefore be used for the treatment of a genetic disease caused by a nonsense-mutation (also called nonsense-mutation-mediated disease). Said nonsense-mutation is defined as a NMD activating mutation.

According to the present invention, a "functional protein" is defined as a truncated or not truncated protein able to have the same cellular functions as the wild-type protein. When the compound according to the invention inhibits NMD, a functional truncated protein may be obtained. When the compound according to the invention promotes readthrough of the PTC, a functional not truncated protein may be obtained. NMD inhibition can be a complete inhibition or only a partial inhibition. In the case of a partial inhibition, the compound according to the invention may not completely suppress the NMD. When the compound according to the invention inhibits NMD partially or totally, the quantity of PTC-containing mRNA increases, so that readthrough promotion by the compound may be favored.

It is known that a small amount of functional protein may be sufficient to enable a normal activity in cells, tissue and/or whole organism. Sometimes a low concentration of functional protein may be enough to obtain a wild-type phenotype in patients. According to the present invention, the term "patient" relates to any kind of living body, more particularly an animal like a mammal and more particularly a human.

The compound according to the invention enables to treat and/or prevent a nonsense-mutation-mediated disease. The compound of the invention enables to delete or attenuate one or more of the disease symptoms.

The compound according to the invention may be administered to any patient as defined hereinabove, said patient being affected by a disease as defined hereinabove. Salts of the compound of formula (I) can be used and are not limited according to the invention. For instance, salts obtained through reacting compound of formula (I) with an alkaline compound are also encompassed in the present invention. Sodium, potassium, calcium, magnesium, ammonium salts and chloride may be obtained through such a reaction. Reaction between the compound of formula (I) and at least an organic or inorganic acid may also provide other salts.

According to the present invention, the term polymorph relates to any mixture of amorphous or crystalline forms of the compound according to the invention.

According to the invention, the disease caused by a nonsense-mutation is not limited. Many nonsense-mutation-mediated diseases have been described. Many organs or functions of the body may be affected by a nonsense-mutation-mediated disease, such as liver or gastro-intestinal function, kidney, cardiovascular, pulmonary, muscular, bone marrow, central nervous system functions, metabolism, organogenesis, inflammation and immunity.

For instance, said nonsense-mutation-mediated disease may be chosen among:
Nonsense-Mutation-Mediated beta-thalassemia, Nonsense-Mutation-Mediated Ehlers-Danlos syndrome, Nonsense-Mutation-Mediated Severe myoclonic epilepsy of infancy, Nonsense-Mutation-Mediated achromatopsia, Nonsense-Mutation-Mediated retinitis pigmentosa, Nonsense-Mutation-Mediated Usher Syndrome Type 1C, Nonsense-Mutation-Mediated Adducted thumb-clubfoot syndrome, Nonsense-Mutation-Mediated Alagille syndrome, Nonsense-Mutation-Mediated Alström syndrome, Nonsense-Mutation-Mediated antithrombin deficiency, Nonsense-Mutation-Mediated Carney complex, Nonsense-Mutation-Mediated Currarino syndrome, Nonsense-Mutation-Mediated Diamond-Blackfan anemia, Nonsense-Mutation-Mediated erythropoietic protoporphyria, Nonsense-Mutation-Mediated Fabry disease, Nonsense-Mutation-Mediated factor XIII deficiency, Nonsense-Mutation-Mediated Fanconi-Bickel syndrome, Nonsense-Mutation-Mediated fish odor syndrome, Nonsense-Mutation-Mediated Gaucher disease, Nonsense-Mutation-Mediated Hereditary hemorrhagic telangiectasia, Nonsense-Mutation-Mediated homocystinuria, Nonsense-Mutation-Mediated Joubert syndrome and related disorders, Nonsense-Mutation-Mediated Krabbe disease, Nonsense-Mutation-Mediated L-2-hydroxyglutaric aciduria, Nonsense-Mutation-Mediated MethylMalonic academia, Nonsense-Mutation-Mediated Niemann-Pick disease, Nonsense-Mutation-Mediated Peters plus syndrome, Nonsense-Mutation-Mediated Townes-Brocks disease, Nonsense-Mutation-Mediated von Willebrand disease, Nonsense-Mutation-Mediated Wiskott-Aldrich syndrome, Nonsense-Mutation-Mediated Kabuki syndrome, Nonsense-Mutation-Mediated Chanarin-Dorfman syndrome, Nonsense-Mutation-Mediated Lecithin:cholesterol acyltransferase deficiency/fish-eye disease, Nonsense-Mutation-Mediated Marfan Syndrome, Nonsense-Mutation-Mediated Mucopolysaccharidiosis, Nonsense-Mutation-mediated Amyloidiosis, Nonsense-Mutation-Mediated Late Infantile Neuronal Ceroid Lipofuscinosis, Nonsense-Mutation-Mediated coenzyme Q10 Deficiency, Nonsense-Mutation-Mediated Peroxisome biogenesis disorders, Nonsense-Mutation-Mediated lysosomal storage disorders, Nonsense-Mutation-Mediated colorectal cancer, Nonsense-Mutation-Mediated congenital enteropeptidase deficiency, Nonsense-Mutation-Mediated Cystic Fibrosis, Nonsense-Mutation-Mediated Hungarian Peutz-Jeghers Syndrome, Nonsense-Mutation-Mediated Jervell and Lange-Nielsen syndrome, Nonsense-Mutation-Mediated Lynch syndrome, Nonsense-Mutation-Mediated microvillus inclusion disease, Nonsense-Mutation-Mediated Peutz-Jeghers syndrome, Nonsense-Mutation-Mediated xanthinuria, Nonsense-Mutation-Mediated Acidosis, Nonsense-Mutation-Mediated Alport syndrome, Nonsense-Mutation-Mediated Bardet-Biedl syndrome, Nonsense-Mutation-Mediated Birt-Hogg-Dube syndrome, Nonsense-Mutation-Mediated Dent's disease, Nonsense-Mutation-Mediated Gitelman syndrome, Nonsense-Mutation-Mediated Hereditary leiomyomatosis and renal cell cancer, Nonsense-Mutation-Mediated hereditary spherocytosis, Nonsense-Mutation-Mediated leber congenital amaurosis, Nonsense-Mutation-Mediated Lysinuric protein intolerance, Nonsense-Mutation-Mediated Nephronophthisis, Nonsense-Mutation-Mediated polycystic kidney disease, Nonsense-Mutation-Mediated pseudohypoaldosteronism, Nonsense-Mutation-Mediated renal hypodysplasia, Nonsense-Mutation-Mediated Sporadic clear cell renal cell carcinoma, Nonsense-Mutation-Mediated type 2 papillary renal cell cancers, Nonsense-Mutation-Mediated Urofacial syndrome, Nonsense-Mutation-Mediated von Hippel-Lindau disease, Nonsense-Mutation-Mediated Wilms' tumor, Nonsense-Mutation-Mediated X-linked Alport syndrome, Nonsense-Mutation-Mediated X-linked hypophosphatemic rickets, Nonsense-Mutation-Mediated Hyperuricaemic nephropathy (juvenile/medullary cystic kidney disease), Nonsense-Mutation-Mediated Tuberous sclerosis, Nonsense-Mutation-Mediated Nephrotic syndrome/congenital nephrotic syndrome, Finnish type Nonsense-Mutation-Mediated Nephrotic syndrome, steroid resistant Nonsense-Mutation-Mediated Nephrotic syndrome 3, early onset Nonsense-Mutation-Mediated Nephrotic syndrome/Pierson syndrome, Nonsense-Mutation-Mediated Denys-Drash syndrome, Nonsense-Mutation-Mediated Nephrotic syndrome/ Schimke immuno-osseous dysplasia, Nonsense-Mutation-Mediated Primary glucocorticoid resistance, Nonsense-Mutation-Mediated X-linked hypophosphatemia, Nonsense-Mutation-Mediated Primary hyperoxaluria type 1, Nonsense-Mutation-Mediated pseudohypoaldosteronism type 1, Nonsense-Mutation-Mediated proximal renal tubular acidosis, Nonsense-Mutation-Mediated Abetalipoproteinemia and Homozygous Familial Hypobetalipoproteinemia, Nonsense-Mutation-Mediated Alpers syndrome, Nonsense-Mutation-Mediated carbamyl phosphate synthetase I deficiency, Nonsense-Mutation-Mediated Cholesteryl Ester Storage Disease, Nonsense-Mutation-Mediated citrin deficiency, Nonsense-Mutation-Mediated Dubin-Johnson syndrome, Nonsense-Mutation-Mediated erythropoietic protoporphyria, Nonsense-Mutation-Mediated Factor V deficiency, Nonsense-Mutation-Mediated Glycogen storage disease, Nonsense-Mutation-Mediated Hemophilia A (factor VIII Deficiency), Nonsense-Mutation-Mediated Hemophilia B (factor IX Deficiency), Nonsense-Mutation-Mediated hepatocellular carcinoma, Nonsense-Mutation-Mediated Hepatoerythropoietic porphyria, Nonsense-Mutation-Mediated hereditary spastic paraplegias, Nonsense-Mutation-Mediated Hypobetalipoproteinemia, Nonsense-Mutation-Mediated Inherited factor XI deficiency, Nonsense-Mutation-Mediated Maturity-onset diabetes of the young, Nonsense-Mutation-Mediated microcytic anemia and iron deficiency, Nonsense-Mutation-Mediated mitochondrial DNA depletion, Nonsense-Mutation-Mediated mitochondrial DNA depletion syndrome, Nonsense-Mutation-Mediated phenylketonuria, Nonsense-Mutation-Mediated polycystic liver disease, Nonsense-Mutation-Mediated porphyria cutanea tarda, Nonsense-Mutation-Mediated progressive familial intrahepatic cholestasis, Nonsense-Mutation-Mediated Wilson Disease, Nonsense-Mutation-Mediated autosomal dominant hypercholesterolemia, Nonsense-Mutation-Mediated factor XII Deficiency, Nonsense-Mutation-Mediated factor X Deficiency, Nonsense-Mutation-Mediated hypofibrinogenaemia, Nonsense-Mutation-Mediated Afibrinogenaemia, Nonsense-Mutation-Mediated factor VII deficiency, Nonsense-Mutation-Mediated agammaglobulinemia, Nonsense-Mutation-Mediated amegakaryocytic thrombocytopenia, Nonsense-Mutation-Mediated dyserythropoietic anemia type II, Nonsense-Mutation-Mediated Duchenne and Becker Muscular Dystrophy, Nonsense-Mutation-Mediated Centronuclear myopathies, Nonsense-Mutation-Mediated limb girdle muscular dystrophy or Miyoshi myopathy, Nonsense-Mutation-Mediated Ullrich disease, Nonsense-Mutation-mediated Spinal muscular atrophy, Nonsense-Mutation-Mediated dystrophic epidermolysis bullosa, Nonsense-Mutation-Mediated Hailey-Hailey Disease, Nonsense-Mutation-Mediated Herlitz junctional epidermolysis bullosa, and Nonsense-Mutation-Mediated Netherton syndrome.

In one embodiment, the nonsense-mutation-mediated disease is selected from beta-thalassemia, Marfan synfrome, Duchenne Muscular Dystrophy, Becker Muscular Dystrophy, Ullrich disease, Hurler syndrome, cancer, cystic fibrosis, Spinal muscular atrophy, amylosis, LINCL (Late Infantile Neuronal Ceroid Lipofuscinosis), Haemophilia, Alzheimer's disease, Atherosclerosis, Gigantism, Dwarfism, Hypothyroidism, Hyperthyroidism, Obesity, Parkinson's disease, Niemann Pick disease, Family hypercholesterolemia, and retinitis pigmentosa.

Several studies have shown that the compound of Formula (I) is preferably distributed in liver, kidneys and intestine. The lungs, the heart, the muscles and the skin are slightly less exposed by the compound of Formula (I) after oral administration. Considering the physiopathology of the diseases and the affected organs for each disease cited hereinabove, and according to the present invention, the said nonsense-mutation-mediated diseases may be preferably chosen among:

Diseases Affecting the Liver:
Nonsense-Mutation-Mediated Abetalipoproteinemia and Homozygous Familial Hypobetalipoproteinemia, Nonsense-Mutation-Mediated Alpers syndrome, Nonsense-Mutation-Mediated carbamyl phosphate synthetase I deficiency, Nonsense-Mutation-Mediated Cholesteryl Ester Storage Disease, Nonsense-Mutation-Mediated citrin deficiency, Nonsense-Mutation-Mediated Dubin-Johnson syndrome, Nonsense-Mutation-Mediated erythropoietic protoporphyria, Nonsense-Mutation-Mediated Factor V deficiency, Nonsense-Mutation-Mediated Glycogen storage disease, Nonsense-Mutation-Mediated Hemophilia A (factor VIII Deficiency), Nonsense-Mutation-Mediated Hemophilia B (factor IX Deficiency), Nonsense-Mutation-Mediated hepatocellular carcinoma, Nonsense-Mutation-Mediated Hepatoerythropoietic porphyria, Nonsense-Mutation-Mediated hereditary spastic paraplegias, Nonsense-Mutation-Mediated Hypobetalipoproteinemia, Nonsense-Mutation-Mediated Inherited factor XI deficiency, Nonsense-Mutation-Mediated Maturity-onset diabetes of the young, Nonsense-Mutation-Mediated microcytic anemia and iron deficiency, Nonsense-Mutation-Mediated mitochondrial DNA depletion, Nonsense-Mutation-Mediated mitochondrial DNA depletion syndrome, Nonsense-Mutation-Mediated phenylketonuria, Nonsense-Mutation-Mediated polycystic liver disease, Nonsense-Mutation-Mediated porphyria cutanea tarda, Nonsense-Mutation-Mediated progressive familial intrahepatic cholestasis, Nonsense-Mutation-Mediated Wilson Disease, Nonsense-Mutation-Mediated autosomal dominant hypercholesterolemia, Nonsense-Mutation-Mediated factor XII Deficiency, Nonsense-Mutation-Mediated factor X Deficiency, Nonsense-Mutation-Mediated hypofibrinogenaemia, Nonsense-Mutation-Mediated Afibrinogenaemia, Nonsense-Mutation-Mediated factor VII deficiency, Diseases Affecting the Kidneys:
Nonsense-Mutation-Mediated Acidosis, Nonsense-Mutation-Mediated Alport syndrome, Nonsense-Mutation-Mediated Bardet-Biedl syndrome, Nonsense-Mutation-Mediated Birt-Hogg-Dube syndrome, Nonsense-Mutation-Mediated Dent's disease, Nonsense-Mutation-Mediated Gitelman syndrome, Nonsense-Mutation-Mediated Hereditary leiomyomatosis and renal cell cancer, Nonsense-Mutation-Mediated hereditary spherocytosis, Nonsense-Mutation-Mediated leber congenital amaurosis, Nonsense-Mutation-Mediated Lysinuric protein intolerance, Nonsense-Mutation-Mediated Nephronophthisis, Nonsense-Mutation-Mediated polycystic kidney disease, Nonsense-Mutation-Mediated pseudohypoaldosteronism, Nonsense-Mutation-Mediated renal hypodysplasia, Nonsense-Mutation-Mediated Sporadic clear cell renal cell carcinoma, Nonsense-Mutation-Mediated type 2 papillary renal cell cancers, Nonsense-Mutation-Mediated Urofacial syndrome, Nonsense-Mutation-Mediated von Hippel-Lindau disease, Nonsense-Mutation-Mediated Wilms' tumor, Nonsense-Mutation-Mediated X-linked Alport syndrome, Nonsense-Mutation-Mediated X-linked hypophosphatemic rickets, Nonsense-Mutation-Mediated Hyperuricaemic nephropathy (juvenile/medullary cystic kidney disease), Nonsense-Mutation-Mediated Tuberous sclerosis, Nonsense-Mutation-Mediated Nephrotic syndrome/congenital nephrotic syndrome, Finnish type, Nonsense-Mutation-Mediated Nephrotic syndrome, steroid resistant, Nonsense-Mutation-Mediated Nephrotic syndrome 3, early onset, Nonsense-Mutation-Mediated Nephrotic syndrome/Pierson syndrome, Nonsense-Mutation-Mediated Denys-Drash syndrome, Nonsense-Mutation-Mediated Nephrotic syndrome/ Schimke immuno-osseous dysplasia, Nonsense-Mutation-Mediated Primary glucocorticoid resistance, Nonsense-Mutation-Mediated X-linked hypophosphatemia, Nonsense-Mutation-Mediated Primary hyperoxaluria type 1, Nonsense-Mutation-Mediated pseudohypoaldosteronism type 1, Nonsense-Mutation-Mediated proximal renal tubular acidosis.

Diseases Affecting the Intestine:
Nonsense-Mutation-Mediated colorectal cancer, Nonsense-Mutation-Mediated congenital enteropeptidase deficiency, Nonsense-Mutation-Mediated Cystic Fibrosis, Nonsense-Mutation-Mediated Hungarian Peutz-Jeghers Syndrome, Nonsense-Mutation-Mediated Jervell and Lange-Nielsen syndrome, Nonsense-Mutation-Mediated Lynch syndrome, Nonsense-Mutation-Mediated microvillus inclusion disease, Nonsense-Mutation-Mediated Peutz-Jeghers syndrome, Nonsense-Mutation-Mediated xanthinuria.

Diseases Affecting Several Organs:
Nonsense-Mutation-Mediated beta-thalassemia, Nonsense-Mutation-Mediated Ehlers-Danlos syndrome, Nonsense-Mutation-Mediated Adducted thumb-clubfoot syndrome, Nonsense-Mutation-Mediated Alagille syndrome, Nonsense-Mutation-Mediated Alström syndrome, Nonsense-Mutation-Mediated antithrombin deficiency, Nonsense-Mutation-Mediated Carney complex, Nonsense-Mutation-Mediated Currarino syndrome, Nonsense-Mutation-Mediated Diamond-Blackfan anemia, Nonsense-Mutation-Mediated erythropoietic protoporphyria, Nonsense-Mutation-Mediated fabry disease, Nonsense-Mutation-Mediated factor XIII deficiency, Nonsense-Mutation-Mediated Fanconi-Bickel syndrome, Nonsense-Mutation-Mediated fish odor syndrome, Nonsense-Mutation-Mediated Gaucher disease, Nonsense-Mutation-Mediated Hereditary hemorrhagic telangiectasia, Nonsense-Mutation-Mediated homocystinuria, Nonsense-Mutation-Mediated Joubert syndrome and related disorders, Nonsense-Mutation-Mediated Krabbe disease, Nonsense-Mutation-Mediated L-2-hydroxyglutaric aciduria, Nonsense-Mutation-Mediated MethylMalonic acidemia, Nonsense-Mutation-Mediated Niemann-Pick disease, Nonsense-Mutation-Mediated Peters plus syndrome, Nonsense-Mutation-Mediated Townes-Brocks disease, Nonsense-Mutation-Mediated von Willebrand disease, Nonsense-Mutation-Mediated Wiskott-Aldrich syndrome, Nonsense-Mutation-Mediated Kabuki syndrome, Nonsense-Mutation-Mediated Chanarin-Dorfman syndrome, Nonsense-Mutation-Mediated Lecithin:cholesterol acyltransferase deficiency/fish-eye disease, Nonsense-Mutation-Mediated Marfan Syndrome, Nonsense-Mutation-Mediated Mucopolysaccharidiosis, Nonsense-Mutation-mediated Amyloidiosis, Nonsense-Mutation-Mediated Late Infantile Neuronal Ceroid Lipofuscinosis, Nonsense-Mutation-Mediated coenzyme Q10 Deficiency, Nonsense-Mutation-Mediated Peroxisome biogenesis disorders, Nonsense-Mutation-Mediated lysosomal storage disorders.

Considering that the compound according to Formula (I) can be administered topically, and according to the present invention, the said nonsense-mutation-mediated diseases may be also chosen among the following diseases affecting the skin or the eyes:
Nonsense-Mutation-Mediated achromatopsia, Nonsense-Mutation-Mediated retinitis pigmentosa, Nonsense-Mutation-Mediated Usher Syndrome Type 1C, Nonsense-Mutation-Mediated dystrophic epidermolysis bullosa, Nonsense-Mutation-Mediated Hailey-Hailey Disease, Nonsense-Mutation-Mediated Herlitz junctional epidermolysis bullosa, Nonsense-Mutation-Mediated Netherton syndrome.

Usually, the compound according to the present invention, either alone (in any of the forms described above) or in combination with another active agent, is administered to patients in admixture with one or more pharmaceutically acceptable excipient(s). The excipients are suitably chosen depending on the mode of administration and the excipient influence on the compound's solubility and stability. The galenic form may be also relevant.

Consequently, a second aspect of the invention relates to a pharmaceutical composition for use in the treatment and/or prophylaxis of a genetic disease, said genetic disease being a nonsense-mutation-mediated disease. The pharmaceutical composition according to the invention comprises, as an active ingredient, at least the compound of formula (I) and one or more pharmaceutically acceptable excipient(s). The composition according to the present invention contains the compound of the invention and thus has the same toxicological properties as the compound itself. It is furthermore noted that the toxicity of the compound of the invention has already been evaluated for an oral administration; the toxicity of an injectable formulation should not differ since what is assessed is the toxicity of the molecule itself optionally metabolised in blood. Accordingly, the composition of the invention can be quickly used and commercialised as a drug.

According to one embodiment, the composition according to the invention can be injected. In this case, the excipient is liquid. The active molecule is dissolved or suspended in the excipient. However, the composition according to the invention is not limited to this type of composition.

The present invention also relates to a pharmaceutical composition as described herein above, further comprising a readthrough agent. The readthrough agent is able to promote the PTC readthrough. The PTC is harbored in the mRNA coming from the transcription of the gene harboring said nonsense mutation. The inventors have observed a synergic effect between the compound of the invention and at least one particular PTC readthrough molecule.

Advantageously, the readthrough agent is 3-[5-(2-fluorophenyl)-1,2,4-oxadiazol-3-yl] benzoic acid (PTC124 disclosed in WO 2004/091502). This readthrough agent is not very efficient and strong doses have to be administered to patients (16 to 40 mg/kg/day). The synergism between this readthrough agent and the compound according to the invention may enhance the activity of said readthrough agent in some cases. Accordingly, lower doses of said readthrough agent are needed.

Accordingly, another aspect of the invention relates to a combination of (i) a compound of formula (I):

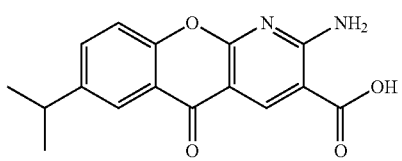

or a salt, solvate, clathrate, hydrate or polymorph thereof, and
(ii) 3-[5-(2-fluorophenyl)-1,2,4-oxadiazol-3-yl] benzoïc acid. The active pharmaceutically agents (i) and (ii) can be administered simultaneously, sequentially or over a period of time.

However, according to the invention, any other readthrough agent may also be mixed or combined with the compound according to the present invention or with the combination PTC124/compound of Formula (I). This readthrough agent is thus included in the composition according to the invention. The aforementioned readthrough agent may also be separately conditioned in order to be administrated with the molecule of the invention, at the same time or according to a delayed administration.

The Man skilled in the Art is able to determine whether a disease is caused by a nonsense-mutation. It is possible, for a given protein, to study whether said protein concentration is relevant towards a disease. The Man skilled in the Art is able to determine whether a given disease caused by a too low protein concentration is a nonsense-mutation-mediated disease by following the hereinafter mentioned steps:

Identification of the gene coding for said given protein and identification of the mRNA coming from said gene transcription; and Comparison of normal genes or normal mRNAs with genes and mRNAs coming from a patient suffering from said disease.

The present invention also relates to a method for determining whether there is a nonsense-mutation harbored in a given gene. This given gene is transcribed into mRNA. The transcribed mRNA harbors a FTC and codes for a given known protein. According to the method of the present invention, Patient's cells are incubated with the compound or a composition of the invention in order to obtain RNA synthesis;

Synthesized RNAs and/or proteins are extracted from the cells and purified;

Purified RNAs are then reverse-transcribed and amplified in order to enable RNA quantitation.

In one embodiment the patient's cells are cells from an organ thought to be affected by the nonsense-mutation or cells differentiated from induced pluripotent stem cells issued from the patient. In another embodiment an increased quantity of purified RNAs and/or proteins indicates NMD inhibition and/or readthrough and therefore the presence of a nonsense-mutation.

The method according to the invention therefore enables to determine whether the genetic disease is at least partially caused by a nonsense mutation. Accordingly, this enables treatment adjustment.

In another aspect, the invention relates to a method of assessing whether the compound of formula (I) or a pharmaceutical composition containing it is efficient in treating a patient diagnosed with a nonsense-mutation-mediated genetic disease, said method comprising the steps of:

treating the patient with said compound or said composition;

observing at least one disease marker in the patient, or extracting synthesized RNAs and/or proteins from said patient cells wherein a modification of the disease marker(s) or an increased quantity of purified RNAs and/or proteins indicates NMD inhibition and/or readthrough, hence that the treatment is efficient.

A disease marker may be the protein (truncated or not) which is normally not synthesized because of the PTC. A disease marker may also be any other substance involved in the disease mechanism and particularly any substance usually used for the diagnosis of the disease. For instance, in the case of hemophilia A, a marker may be Factor VIII, in the case of hemophilia B, a marker may be factor IX, in the case of Duchene muscular dystrophy, a marker may be dystrophin itself, in the case of cystic fibrosis, a marker may be the concentration of chloride that is excreted in sweat.

The present invention also relates to the use of the compound of Formula (I) in the manufacture of a drug for treating and/or preventing nonsense-mutation-mediated genetic diseases.

The present invention also relates to a therapeutic method for treating nonsense-mutation-mediated genetic disease comprising the step of administering a compound according to formula (I) and/or a pharmaceutical composition according to the invention.

The present invention, its features and advantages will be explained on the basis of the following Examples and Figures, wherein.

Figure 10:
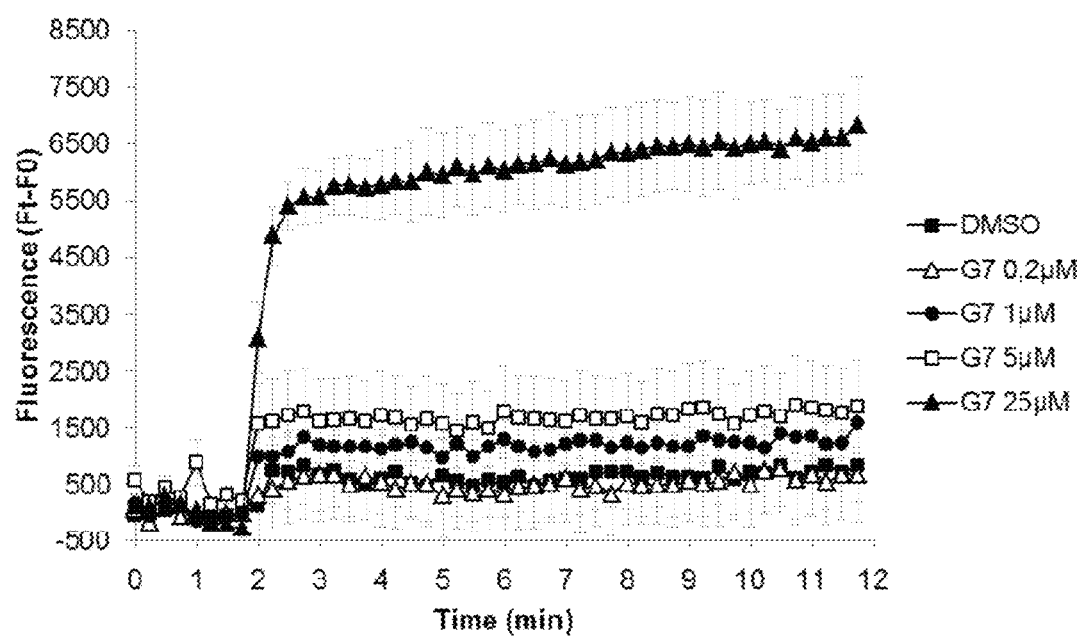
Figure 11A:
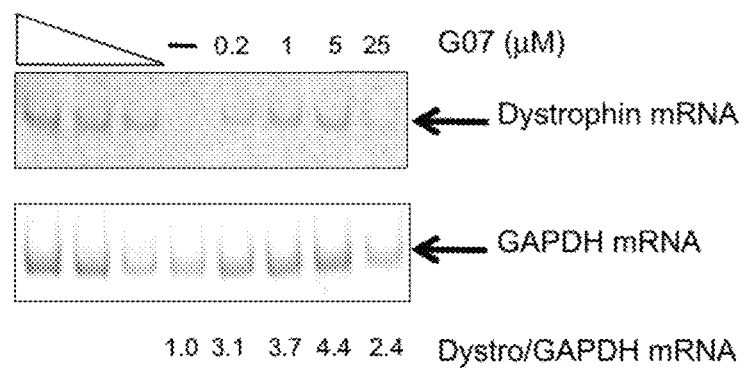
Figure 11B:
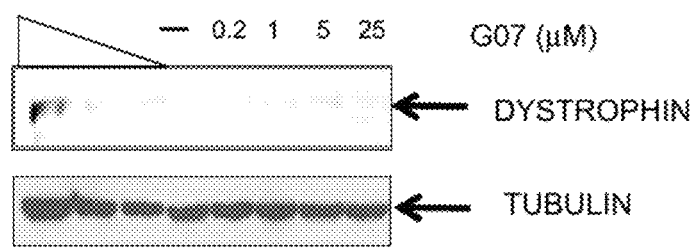

FIG. 10 shows the dose-response effect of the compound of the invention on iodide efflux in 6-CFSMEo⁻ cells (cells coming from a patient suffering from nonsense-mutation mediated cystic fibrosis); and FIGS. 11 a and b show the effect of several doses of the compound of the invention on the expression of PTC-containing dystrophin gene in DMD cells coming from a patient suffering from nonsense-mediated Duchenne muscular dystrophy.

EXAMPLES

In the following examples the compound of formula (I) will be referred to as molecule G07. Related compounds G08 and G09 were also used in tests.

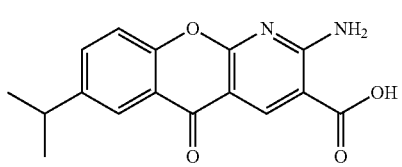

G07

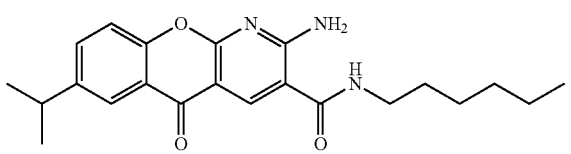

G08

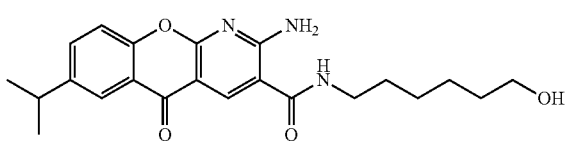

G09

Example 1: Determination of NMD Inhibition by Using Firefly Luciferase

The presence of one of the following UPF proteins (UPF1, UPF2, UPF3 (also called UPF3a) or UPF3X (also called UPF3b)) on the 3'UTR part of an mRNA, activates NMD on this particular mRNA. When an UPF protein is located downstream from a normal stop codon, said normal stop codon is recognized as a PTC. Consequently, the mRNA comprising the UPF protein will be degraded through NMD.

HeLa cell-line expressing Firefly luciferase mRNA were used. Firefly luciferase mRNA harbors MS2 binding sites in the 3'UTR. The above-mentioned cells further contain a fusion protein which consists in said MS2 protein and one of the four UPF proteins. This fusion protein enables UPF positioning downstream from the normal stop codon (i.e. on the 3'UTR part of this mRNA). Accordingly, the normal stop codon is recognized as a PTC. Consequently, NMD is activated and degrades Firefly luciferase mRNA.

Luciferase activity in the above-mentioned cells is thus directly linked to NMD activity. A low luminescence indicates that NMD is activated and a high luminescence indicates NMD inhibition. In the presence of G07, luciferase activity is higher than in control wells. This shows the NMD inhibiting activity of G07.

HeLa cells were cultured in DMEM (Gibco) supplemented with 10% FBS and containing 10 μmol/l of G07.

Since G07 inhibits NMD regardless the type of UPF protein located on mRNA, G07 can be considered as a general NMD inhibitor.

Example 2: Beneficial Effect of G07 on Cells from Patient Harboring Nonsense-Mutation-Mediated Lung Cancer Calu-6 cells (ATCC) harbor a UGA PTC at the codon 196 of the P53 gene. These Calu-6 cells have been isolated from a lung-cancer patient. RNAs of said Calu-6 cells were reverse transcribed and amplified through PCR (RT-PCR) in the presence of a radioactive labeling nucleotide in order to measure P53 mRNA and GAPDH mRNA levels (GAPDH being used as a loading control). Calu-6 cells harbor a nonsense mutation in the P53 gene. Accordingly, the P53 gene is not expressed in Calu-6 cells because of the NMD activity on P53 mRNA. Amplified reverse transcribed mRNAs were loaded on an acrylamide gel and submitted to electrophoresis. Acrylamide gel was then dried on Whatman paper and applied on a phosphoscreen (Kodak). A Personal Molecular Imager (Bic-Rad) was used to quantify amplified radiolabelled species. Calu-6 cells were incubated with growing concentrations of G07 in DMSO during about twenty hours. This was carried out in order to confirm NMD inhibition activity of G07. After incubation, RNAs were purified by using TriReagent (MRC) and then reverse-transcribed into cDNA which can be PCR amplified in presence of a radiolabelled nucleotide. Corresponding results are shown in FIG. 2.

Figure 1:
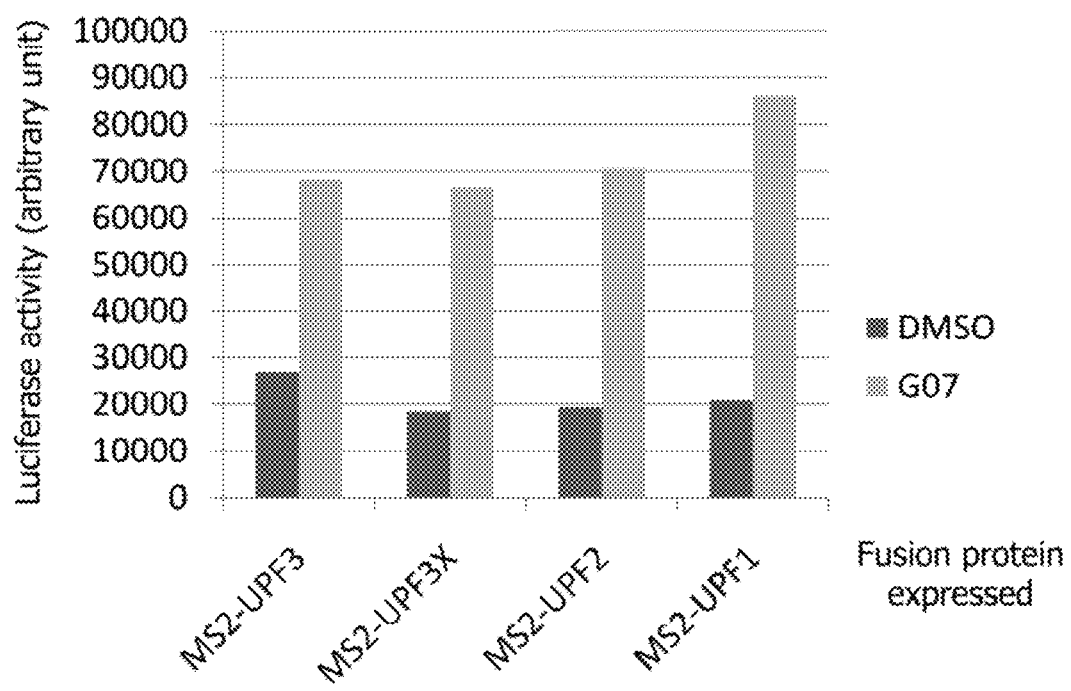
FIG. 1 shows the NMD inhibiting activity of a composition according to the present invention in HeLa cells, using Firefly luciferase.
Figure 2:
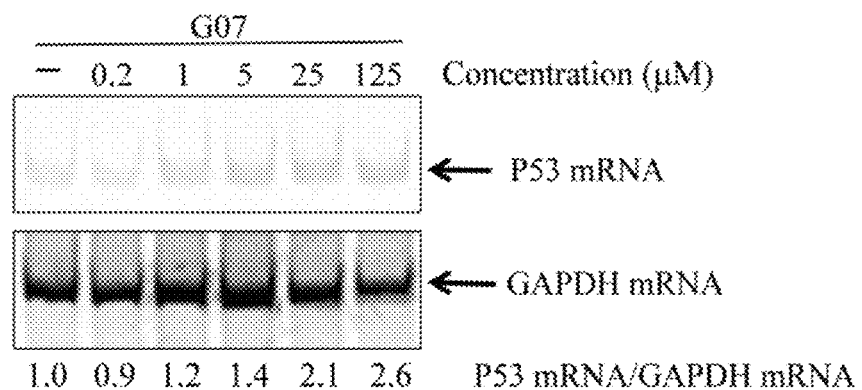
FIG. 2 shows P53 mRNA stabilisation in Calu-6 cells (cells coming from a patient suffering from a genetic nonsense-mediated lung cancer) vs. active molecule concentration, said stabilisation being obtained through NMD inhibition by a composition according to the invention.

FIG. 2 shows an increased quantity of P53 mRNA when the concentration of G07 increases. P53 mRNA is normally degraded via NMD. Thus, an increasing quantity of P53 mRNA results from stabilization thereof. Accordingly, G07 seems to have a dose response activity on NMD mechanism. This experiment confirms NMD inhibiting activity of G07 and further proves that. G07 is able to inhibit NMD towards an endogenous mRNA. GAPDH (Glyceraldehyde 3-phosphate deshydrogenase) mRNA was amplified in order to normalize the measurement of P53 mRNA between two lanes.

Figure 3:
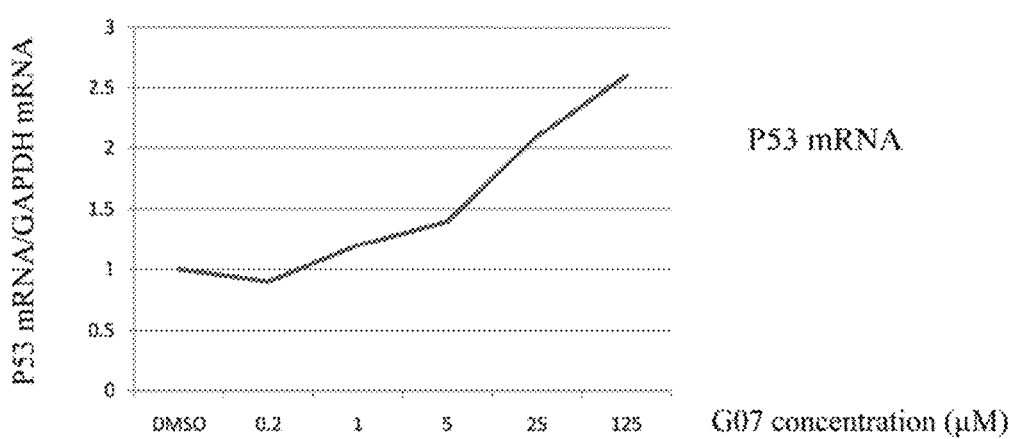
FIG. 3 is a graph showing the ratio P53 mRNA/GADPH mRNA vs. the active molecule concentration of a composition according to the invention.

FIG. 3 shows that the higher the G07 concentration, the greater the amount of P53 mRNA in cells.

Figure 4:
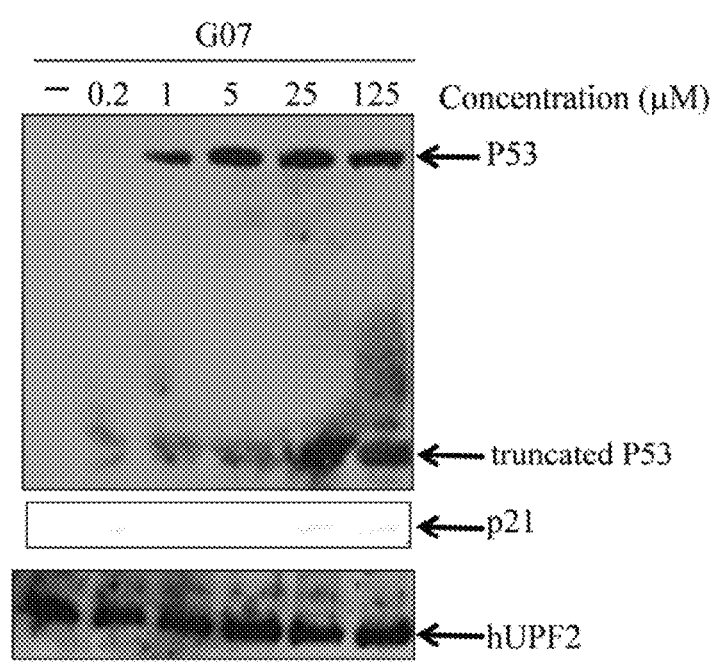
FIG. 4 shows the full-length P53 protein synthesized in Calu-6 cells in the presence of a composition according to the invention.

Moreover, G07 enables the synthesis of a truncated P53 protein and a full-length P53 protein in Calu-6 cells. G07 is thus different from the molecules disclosed in WO 2008/101935. Regarding the molecules disclosed in the above-mentioned document, only the truncated protein has been detected. This result is shown in FIG. 4. Protein extracts of Calu-6 cells incubated or not with G07 were loaded on an electrophoresis gel and then transferred on a nitrocellulose membrane in order to detect P53 protein after incubation with an anti-P53 antibody (an anti-P53 antibody is an antibody directed against the amino terminal part of P53 (Santa Cruz)). The obtained result is shown in FIG. 4. According to FIG. 4, when Calu-6 cells are incubated with G07 during about 20 hours, full-length and truncated P53 proteins are synthesized by cells.

FIG. 4 also shows an analysis of the presence of P21 protein in order to check whether the full-length P53 protein is functional. When P53 protein is synthesized, P53 activates P21 expression. Western-Blot analysis shows the presence of P21 when increasing G07 concentrations are used (25 and 125 µM). Thus, P53 protein synthesized thanks to G07 induces P21 expression as WT P53 protein does. Consequently, the Applicants have thus confirmed that G07 enables the synthesis of a functional full-length P53 protein.

Consequently, G07 enables full-length protein synthesis. G07 may enable PTC readthrough. G07 may also inhibit NMD at a critical stage thereof enabling therefore the full-length protein synthesis. The synthesized full-length protein may be the wild-type protein.

Example 3: In Vivo NMD Inhibition

In KIM mice, MOR gene harbors a NMD-activating nonsense-mutation. MOR gene is expressed in nervous central system. Solutions containing 0.2, 2 or 20 mg/kg of G07 (1Q, 2Q or 3Q respectively) dissolved in DMSO were injected into KIM mice. A control group consists of animals treated with pure DMSO. Animals were then euthanized 6, 24 or 32 hours after injection. RNAs extracted from brain homogenates were purified using TriReagent (MRC) and then analyzed as described with reference to FIG. 2. The difference between the experiments described with reference to FIG. 2 is that in the present case the mRNAs analyzed are the mRNA coding for MOR gene and the mRNA coding for the GAPDH gene used as a control to quantify measured MOR mRNA. The first 3 wells from the left correspond to a half dilution of a sample coming from a wild-type mouse brain. These 3 wells were used to check the PCR conditions which have to be quantitatively useful.

Figure 5:
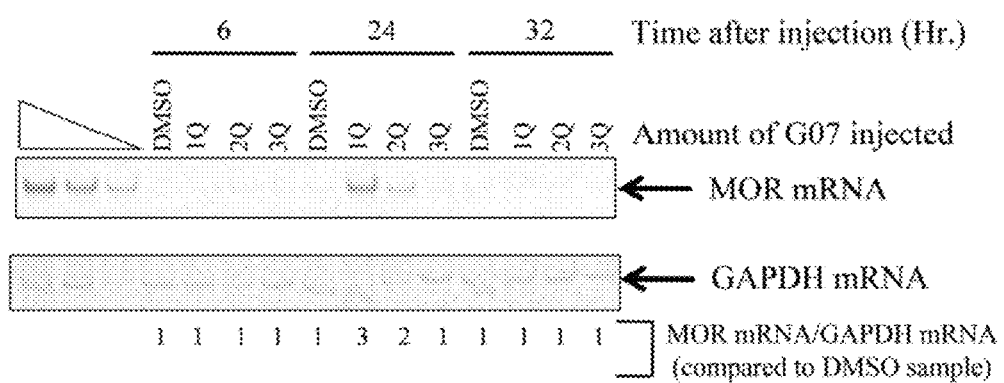
FIG. 5 shows mRNA MOR concentration in mouse brain cells vs. active compound concentration in a mouse model wherein MOR gene harbors a nonsense-mutation.

FIG. 5 shows measurements of mRNA levels of MOR and GADPH (the latter used as a control). The same technique as described with reference to FIG. 2 was used except the fact that RNA comes from KIM mice brains. Some of these KIM mice were injected with G07.

A stabilization of MOR mRNA was observed after 24 hours for 1Q and 2Q concentrations. This indicates NMD inhibition. Hence, this experiment confirms the in vivo NMD inhibition activity of G07.

Example 4: Use of G07 in Combination with a Readthrough Agent

Figure 6:
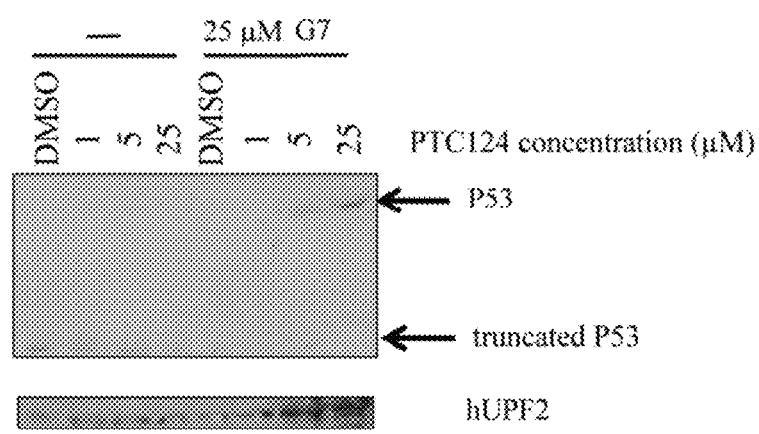
FIG. 6 shows the synergism between the composition of the invention and PTC124 (premature stop codon readthrough agent)

PTC124 (ataluren or 3-[5-(2-fluorophenyl)-1,2,4-oxadiazol-3-yl]benzoïc acid) is a molecule which activates readthrough. This molecule has no NMD inhibiting activity. Calu-6 cells were incubated in DMSO as a control (–), in DMSO solutions containing increasing concentrations of PTC124 and in DMSO solutions containing increasing concentrations of PTC124 and further 25 µM of G07. Protein extracts of these cells were prepared 24 hours after the start of the incubation and analyzed via Western Blot. According to the Western-blot as shown in FIG. 6 (i.e. after a very short exposition time) full-length P53 protein can be observed only in cells incubated with a medium containing G07 and PTC124. Thus, the two molecules have synergism when used together. FIG. 6 shows that incubating Calu-6 cells in a medium containing a mixture of PTC124 and G07 improves full-length P53 protein synthesis. This improvement is more efficient than the improvement obtained for each molecule separately used. Thus there is a synergism between G07 and PTC124.

Example 5: NMD Inhibition in IB3 (Cystic Fibrosis Model)

IB3 cells harbor a FTC in position 1282 in place of the tryptophan codon of the CFTR gene.

IB3 cells (ATCC) were incubated in DMSO solutions containing pure DMSO (as a control) or increasing G07 concentrations, respectively, during 20 hours.

Figure 7:
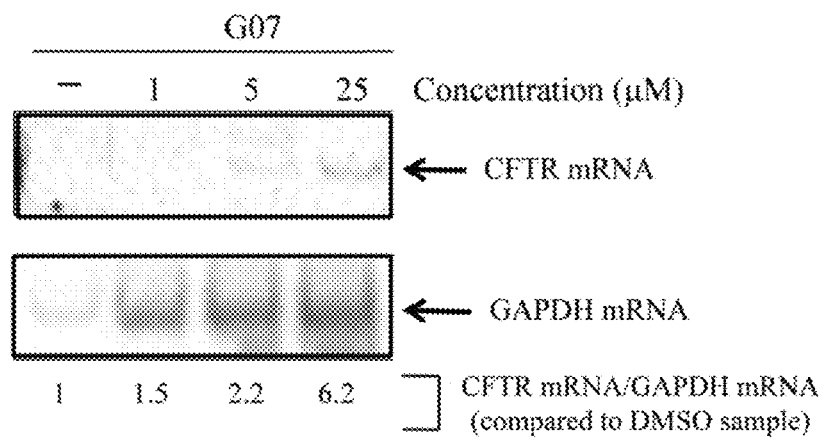
FIG. 7 shows CFTR mRNA in IB3 cells (cells coming from a patient suffering from nonsense-mutation mediated cystic fibrosis) incubated with compositions according to the present invention having different active molecule concentrations.

RNAs obtained after incubation were purified and a RT-PCR was performed to measure the amount of CFTR mRNA (containing a PTC) and the amount of GADPH mRNA (used as a control). On the basis of the ratio amount of CFTR mRNA/amount of GAPDH mRNA shown, we can conclude that there is an increased stabilization of CTFR mRNA. This result is shown in FIG. 7. This result confirms the NMD inhibiting activity of G07 as already observed in Calu-6 cells. This experiment shows the ability of G07 to inhibit NMD in several and different types of cell.

Figure 8:
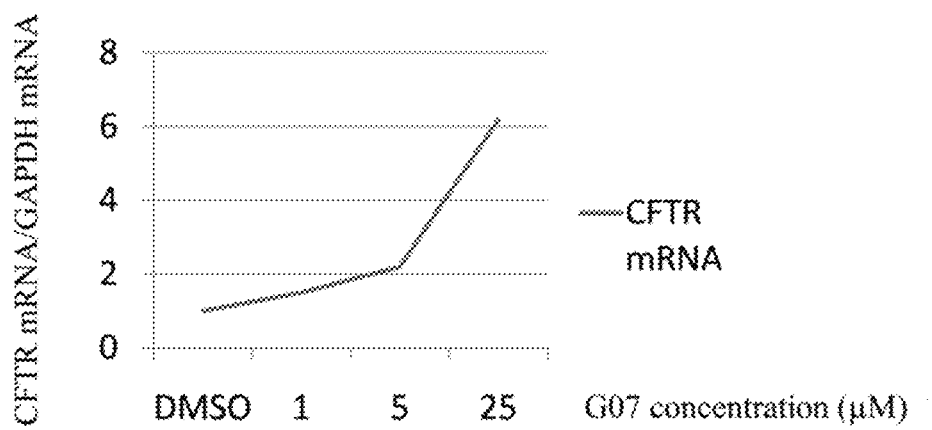
FIG. 8 shows CFTR mRNA concentration in IB3 cells incubated in the presence of a composition according to the present invention vs. the active molecule concentration of said composition.

As shown in FIG. 8, the greater the concentration of G07 in the culture medium, the more stabilized the mRNA normally degraded through NMD.

This indicates that. NMD inhibition depends on the concentration of G07 in the culture medium.

Figure 9:
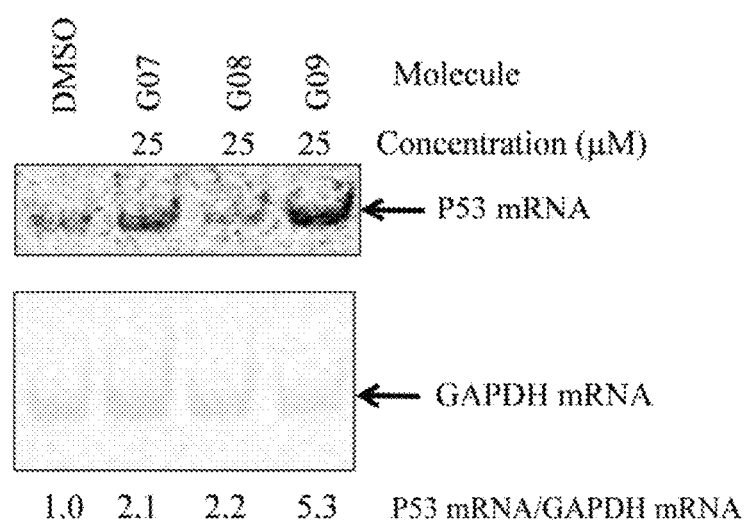
FIG. 9 shows P53 mRNA in Calu-6 cells incubated with three different compositions, each composition containing 25 μmol/l of active compound according to the invention.

Example 6: NMD Inhibition Activity of Compositions Containing G07 G08 and G09, Respectively Calu-6 cells were incubated with compositions containing 25 µM of G07, G08 and G09, respectively. The same experiment as previously described in reference with NMD inhibition confirmation in Calu-6 cells was performed with each composition. Results are shown in FIG. 9. Each 25 μM composition inhibits NMD and enables a stabilization of P53 mRNA in Calu-6 cells.

Example 7: Dose-Response Effect of G07 on Iodide Efflux in 6-CFSMEo⁻ Cells (Cells Coming from a Patient Suffering from Cystic Fibrosis)

6-CFSMEo- cells harbor a PTC in place of the glutamine 2 codon of the CFTR gene.

6-CFSMEo⁻ cells were seeded in 96-well plates and loaded overnight with 10 mM of the halide-sensitive fluorophore dye 6-methoxy-N-(3-sulfopropyl)-quinolinium (SPQ, Invitrogen). Cells were washed twice with iodide buffer (135 mM NaI, 2.4 mM $K_2HPO_4$, 0.6 mM $KH_2PO_4$, 1 mM $MgSO_4$, 1 mM $CaSO_4$, 10 mM dextrose and 10 mM Hepes, pH 7.3) and then incubated in iodide buffer for 30 min. After basal fluorescence was measured for 2 min, the iodide buffer was replaced with nitrate buffer (with 135 mM $NaNO_3$ instead of NaI) containing 20 μM of forskolin and 200 μM of IBMX, and fluorescence was further measured for 10 minutes. The fluorescence intensities were measured every 15 seconds using the Tristar LB 941 microplate reader (Berthold) equipped with a 340 nm excitation filter and a 450 nm emission filter. The arrow in FIG. 10 shows the addition of nitrate buffer containing 20 μM of forskolin and 200 μM of BMX, as explained above. G07 concentrations used were 0.2 μM, 1 μM, 5 μM and 25 μM, respectively. The increase in iodide efflux is shown as mean±SEM from at least four independent assays. It refers to the fluorescence at the reading time; F0 refers to the average fluorescence before addition of the above-mentioned nitrate buffer containing 20 μM of forskolin and 200 μM of IBMX.

On the basis of the results shown in FIG. 10, it is clear that G07 has a dose-response effect on 6-CFSMEo– cells and leads to the synthesis of functional CFTR protein from a PTC-containing CFTR gene.

Example 8: Effect of G07 on the Expression of PTC-Containing Dystrophin Gene in Cells from a Patient Suffering from Nonsense-Mutation-Mediated Duchenne Muscular Dystrophy (i.e. DMD Cells)

As regards the results of FIG. 11 a, DMD cells were incubated with increasing amounts of G07 molecule or as a control with DMSO. RNAs were purified using RNazol reagent (MRC) and reverse transcribed using Superscript. II (Life technologies) and random hexamer. PCR using radiolabelled CTP was performed in order to amplify either dystrophin or GAPDH cDNA. Amplification products were loaded on 5% polyacrylamide gel. The gel was then dried and exposed on phosphoscreen in order to allow quantification of each amplification species by Personal Molecular Imager (Biorad).

As regards the results of FIG. 11 b, DMD cells were incubated with increasing amounts of G07 molecule or as a control with DMSO. Protein extracts from these cells were loaded on 10% SDS-PAGE and transferred on nitrocellulose membrane. Nitrocellulose membrane was then exposed to primary antibody (either anti-dystrophin antibody raised against the amino-part of dystrophin protein (Santa-Cruz), or anti-tubulin antibody in order to specify the loading protein amount of each lane.

FIGS. 11 a and b show that G07 is able to rescue the expression of PTC-containing dystrophin gene in cells coming from a patient suffering from nonsense-mediated Duchenne muscular dystrophy.

As shown in FIG. 11 a, increasing amounts of G07 lead to the stabilization of dystrophin mRNA. This result is obtained through RT-PCR. The maximum of efficacy is obtained at a concentration of 5 μM.

As shown in FIG. 11 b, increasing amounts of G07 lead to the synthesis of dystrophin protein (results obtained through Western-blot with an antibody raised against the amino-terminal part of dystrophin protein). The maximum of G07 efficacy is 5 μM which is consistent with the results shown in FIG. 11 a.

The invention claimed is:

1. A method of treating a nonsense-mutation-mediated lysosomal storage disorder, which comprises administering as sole active ingredient to a subject in need thereof a compound of formula (I):

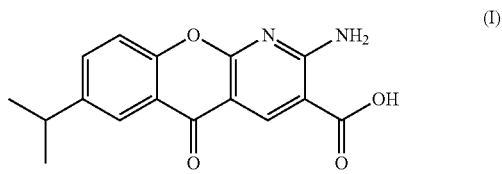 [SMILES: CC(C)c1ccc2oc3nc(N)c(C(=O)O)cc3c(=O)c2c1]

or a salt, solvate, clathrate, hydrate or polymorph thereof.

2. The method of claim 1, wherein the compound of formula (I) is administered through injection.

3. A method of treating a nonsense-mutation-mediated lysosomal storage disorder, which comprises administering to a subject in need thereof a compound of formula (I):

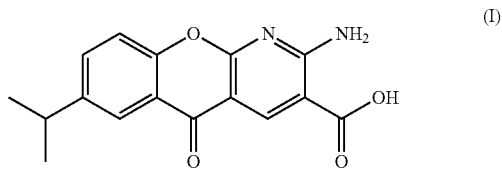 [SMILES: CC(C)c1ccc2oc3nc(N)c(C(=O)O)cc3c(=O)c2c1]

or a salt, solvate, clathrate, hydrate or polymorph thereof, in combination with an agent able to enhance readthrough of the mRNA premature stop-codon, said mRNA premature stop-codon coming from the translation of the gene comprising the nonsense-mutation.

4. The method of claim 3, wherein said agent is 3-[5-(2-fluorophenyl)-1,2,4-oxadiazol-3-yl] benzoic acid.

5. The method of claim 3, wherein the compound of formula (I) and the agent are administered simultaneously.

6. The method of claim 3, wherein the compound of formula (I) and the agent are administered sequentially.

7. The method of claim 6, wherein the compound of formula (I) and the agent are administered over a period of time.

* * * * *